United States Patent [19]

Frye

[11] Patent Number: 4,694,829
[45] Date of Patent: Sep. 22, 1987

[54] THERAPEUTIC STUFFED TOY

[76] Inventor: Ruth E. Frye, 505 S. Main, Lindsay, Okla. 73052

[21] Appl. No.: 817,901

[22] Filed: Jan. 9, 1986

[51] Int. Cl.<sup>4</sup> ............................ A61F 7/08; A61F 7/10
[52] U.S. Cl. .................................... 128/399; 128/403; 383/901
[58] Field of Search ........................ 128/399, 402, 403; 126/204; 62/530; 383/901

[56] References Cited

U.S. PATENT DOCUMENTS

| | | | |
|---|---|---|---|
| 853,639 | 5/1967 | Hincks | 383/901 X |
| 1,558,278 | 10/1925 | Phillips | 383/901 X |
| 1,927,751 | 9/1933 | Mensi | 128/403 X |
| 2,203,591 | 6/1940 | Brown | 62/530 |
| 2,515,298 | 7/1950 | Feldman | 126/204 |
| 3,885,403 | 5/1975 | Spencer | 128/399 X |
| 4,204,110 | 5/1980 | Smit et al. | 128/399 X |
| 4,503,560 | 3/1985 | Bourne | 383/901 X |

Primary Examiner—Anton O. Oechsle
Attorney, Agent, or Firm—Crutsinger & Booth

[57] ABSTRACT

A therapeutic stuffed toy according to the present invention comprises an outer stuffed fabric member, such as a "teddy bear," having an interior pocket containing a hermetically sealed container of a non-toxic liquid whose freezing point is below that of water and boiling point is above that of water. The container is removable from the pocket through an opening in the outer fabric member for the purpose of first preparing it for use by heating when the toy is to be used as a hot "compress", and cooling when the toy is to be used as a cold "compress". In another embodiment, the thermal material is in the form of salt dampened with propylene glycol or water.

13 Claims, 2 Drawing Figures

THERAPEUTIC STUFFED TOY

TECHNICAL FIELD

The present invention relates to a stuffed fabric toy having within an interior pocket thereof a hermetically sealed container of liquid or solid particulate material to form a heat sink, and is suitable for the contacting application of heat or cold to the person of babies and children for psychological or therapeutic purposes. The container is removable for the purpose of first preparing it for use by heating when the toy is to be used as a hot "compress," and cooling with the toy is to be used as a cold "compress."

BACKGROUND INFORMATION

Various modifications of a therapeutic "compress" of the type employing a resilient container or envelope in which is hermetically sealed a low freezing point and/or high boiling point liquid are disclosed in U.S. Pat. Nos. 1,964,655; 2,375,087; 2,547,886; 2,697,424; 2,715,315; 2,749,914; 2,783,806; 3,092,112; and 3,349,825.

In particular, U.S. Pat. No. 3,092,112 discloses the use of 1,2-propane-diol (also known as "propylene glycol") sealed within thermoplastic envelope materials of the halogen modified type. 1,2-propane-diol is stated to be particularly advantageous in that it has a low vapor pressure at ambient temperatures, a high boiling point, is liquid at sub-zero temperatures, is non-toxic, resists mold formation and is substantially chemically inert with thermoplastic envelope materials of the halogen modified type for prolonged periods of time. Disclosed envelope materials include elastomers, as well as thermoplastics, such as polyvinyl chloride. It is pointed out that the liquid can be dyed, and that the envelope material may or may not be transparent in color.

The prior art also discloses various structures in which the envelope may be packaged or placed, such as a jacket (U.S. Pat. No. 2,403,676), or shapes that the envelope may take, such as a bag shaped to conform to the forehead of a person (U.S. Pat. No. 1,964,655).

Unlike the present invention, however, these "antiseptic-appearing" prior art structures, offer little to sustain the limited attention of children to continuously holding the compress in place once it is prepared for use, by heating, or cooling, as appropriate. The psychological soothing and calming effect of even conventional stuffed fabric toys upon children is well known. For this reason, the present invention is doubly advantageous for use with children with its added medically therapeutic value.

Also, since in the present invention, an outer fabric layer or member effectively "insulates" from the user the envelope or container, after it has been prepared for use and inserted into an interior pocket of the toy, through an opening in the outer layer or member of the toy, the prior art problem of too direct an application of the envelope, or container, to the skin, which can in certain instances otherwise cause burning due to extreme heat or cold of the liquid, is solved.

Further, in this manner also solved is the prior art problem of too quick of a dissipation of the heat or cold, as the case may be, of the liquid within the envelope or container.

Finally, the prior art problem of preventing access to the liquid during use by children is solved.

SUMMARY OF THE INVENTION

The present invention comprises a toy, whose outer layer or member is made of conventional material, such as a machine washable acrylic plush fabric, and may take the shape of a human or animal figure, or a cartoon character, for example. Numerous other shapes are, of course, also possible. The outer layer or member is stuffed with a conventional insulating material having a relatively low coefficient of thermal conductivity, such as polyester fill or polyurethane foam. When in use, a hermetically sealed envelope or container containing a liquid or solid particulate material is, placed into an interior pocket of the toy to form a heat sink.

The pocket forms a cavity inside the body of the figure and prevents the insulating material from coming out when it is opened.

The pocket is preferably situated on a side of the outer member corresponding to midway up where a side seam of a conventional toy animal figure is located.

In a first embodiment of the invention, the container is filled with liquid which preferably has a low freezing point and a high boiling point. In a second embodiment, the container is filled with a solid particulate material dampened with liquid. In a third embodiment, the container is filled with solid particulate material such as metallic spheres or table salt.

The container is removable from the pocket for the purpose of first preparing it for use by heating when the toy is to be used as a hot compress, and cooling when the toy is to be used as a cold compress. The opening in the outer member is openable and closable by a conventional means such as a zipper, or a mating fastener means such as a strip of loop fastener material which engages a corresponding strip of hook fastener material, for example. When the pocket is closed, the outer fabric layer or member effectively "insulates" from the user the envelope or container of liquid. The opening and closing means is designed to be "child-proof," however, the liquid within the container is non-toxic to prevent injury to a child if access to it is gained and it is ingested.

BRIEF DESCRIPTION OF THE DRAWINGS

For a better understanding of the preferred embodiment of the present invention, reference may be had to the following detailed description taken in conjunction with the accompanying drawings in which.

DESCRIPTION OF A PREFERRED EMBODIMENT

Figure 1:
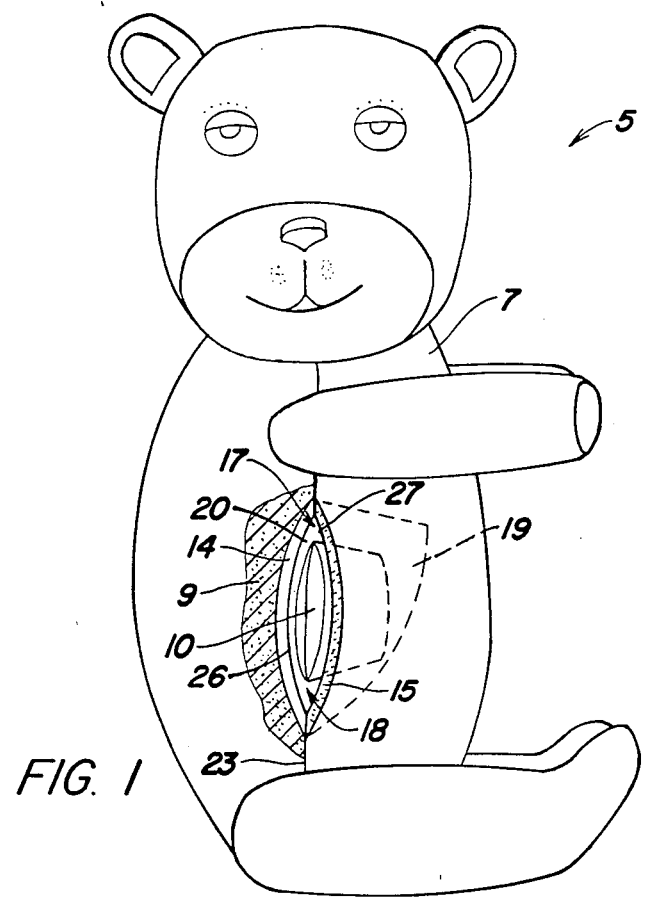
FIG. 1 is a side elevation view of a therapeutic toy constructed in accordance with the present invention, with part of the wall of the outer member broken away to show the insulating material, and, with the pocket opened, shows the proper positioning for use of the container or envelope.
Figure 2:
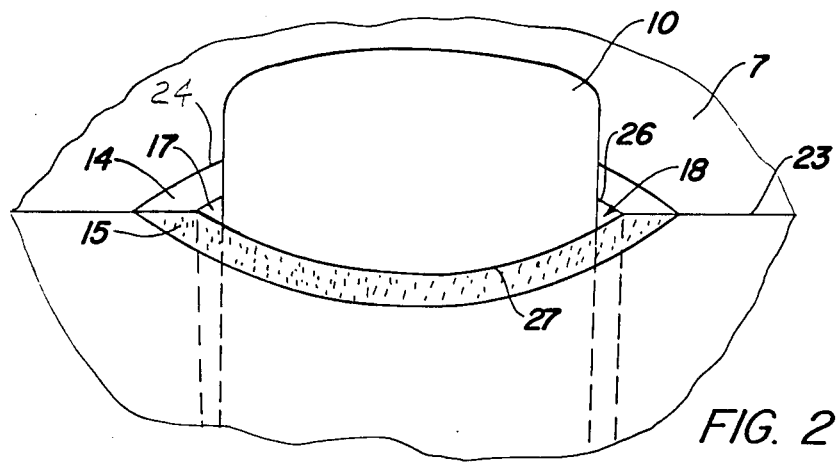
FIG. 2 is a fragmentary view partially in section shown in greater detail the pocket structure and opening and closing means of the therapeutic toy of FIG. 1.

Referring to FIG. 1 of the drawings, the numeral 5 generally designates a toy, whose outer member 7 is shown in the shape of an animal figure, such as a "teddy bear." Numerous other shapes are, of course, also possible. Outer member 7 is preferably constructed of a machine washable acrylic plush fabric. Toy 5 is stuffed with insulating material 9 having a relatively low coefficient of thermal conductivity, such as polyester fill or polyurethane foam. Hermetically sealed envelope or container 10, which is preferably constructed of a halogen modified thermoplastic material, contains non-toxic liquid 11 or solid particulate material, such as table salt, dampened with liquid. The liquid preferably has a low freezing point and a high boiling point. However, water may be employed.

If it is deemed expedient to do so solid particulate material such as small metallic spheres or granular table salt may be used in lieu of the liquid.

In the preferred embodiment the container is partially filled with ordinary table salt and dampened with a small amount of propylene glycol which has been treated to render it non-toxic. Since the bag is impervious, the salt dampened with propylene glycol will remain soft and pliable and retain its heat conducting capabilities. Further, in the event that the container becomes punctured, the small volume of propylene glycol which has been used to dampen the salt will be absorbed in the stuffing material around the outside of the container to minimize the possibility that any liquid will be ingested by a child.

As shown in FIG. 1, container 10 is positioned for use by placing it into pocket 18 through opening 17 in outer member 7. In the embodiment shown, pocket 18 comprises a generally hemispherically shaped piece of fabric folded in two to form first pocket panel 19 and second pocket panel 20, whose curved edges are suitably attached together, as by stitching. The straight line edges of pocket panels 19 and 20 are, in the embodiment shown, substantially coextensive with the edges of opening 17 in outer member 7, which in this example, takes the form of a slit, and are conventionally secured, as by stitching, to downwardly extending sides, 26 and 27, of opening 17, which are seamed together to form the side seam 23 for the remainder of their length. As shown, strip member 24 is attached to outer member 7 on one side of opening 17. Flap 23 is integral with strip member 24 and extends outwardly therefrom sufficiently that strip 14 of hook fastener material, on its underside, can overlap and mate with strip 15 of loop fastener material which is attached on the opposite side of opening 17. Other conventional opening and closing means, such as a zipper, snaps, buttons, or ties may be employed if it is deemed expedient to do so. Container 10 is removable from the pocket for preparing it for use by heating when toy 5 is to be used as a hot compress, or cooling when toy 5 is to be used as a cold compress.

The closure means is designed to be "child-proof," however, as previously mentioned, liquid 11 within container 10 is non-toxic to prevent injury to a child if access to it is gained and it is ingested. Seams of the stuffed toy may be sewn to permanently close the opening if it is deemed expedient to do so.

Further, it should be readily apparent that opening 17 might be formed at a location other than in a side of the body of toy 5. For example, if the figure assumed the shape of a frog or a cartoon character having a large mouth, the opening 17 could be formed in the mouth.

What is claimed is:

1. A therapeutic toy for contacting application to the human body comprising: an outer body member having an outer configuration of a figure; absorbent insulation having a pocket formed therein in said outer body member; a container in said pocket having hermetically sealed therein a moisture laden material to form a heat sink, said moisture laden material and said container being substantially inert with respect to each other, and said container being substantially non-pervious to said moisture laden material, said absorbent insulation around said pocket being adapted to absorb the volume of moisture contained in said moisture laden material.

2. A therapeutic toy according to claim 1 wherein said moisture comprises: liquid having a freezing point below that for water and a boiling point above that for water.

3. A therapeutic toy according to claim 2 wherein the liquid is 1,2 propane-diol.

4. A therapeutic toy according to claim 1 wherein the container is an envelope constructed of a halogen modified thermoplastic material.

5. A therapeutic toy according to claim 1 wherein the body member has the configuration of an animal.

6. A therapeutic toy according to claim 1 wherein the body member has the configuration of a teddy bear.

7. A therapeutic toy according to claim 1, wherein said moisture laden material comprises particulate material dampened with propylene glycol material.

8. A therapeutic stuffed toy for contacting application to the human body to transfer heat comprising: an outer body member having an outer configuration of a doll figure and having a cavity formed therein; a container in said cavity; particulate material dampened with liquid hermetically sealed in said container, said container being substantially impervious to said material to permit heating or cooling of said material in said container; and absorbent insulation around said container to control the rate of heat transferred to or from said container, the volume of liquid used to dampen said particulate material being less than that which will be absorbed by said absorbent insulation in the event that said container becomes punctured to prevent ingestion of said liquid.

9. A therapeutic toy according to claim 8, wherein said particulate material comprises salt.

10. A therapeutic toy according to claim 8, wherein the liquid comprises propylene glycol.

11. A therapeutic toy according to claim 8, wherein the liquid is water.

12. A therapeutic toy positionable in heat exchange relation to the human body comprising: an outer body member having an outer configuration of an animal-like figure and having an inner cavity; a container in said inner cavity; non-toxic particulate material dampened with liquid having a freezing point below that for water and a boiling point above that for water in said container, said material and said container being substantially inert with respect to each other, and said container being substantially impervious to said material, said container being hermetically sealed to allow heating or cooling of material in said container to form a heat sink; and insulation material around said container to control the rate of heat transfer to and from said material.

13. A therapeutic toy positionable in heat exchange relation to the human body comprising: an outer body member having an outer configuration of an animal-like figure and having an inner cavity; a container in said inner cavity; nontoxic material comprising salt dampened with propylene glycol in said container, said material and said container being substantially inert with respect to each other, and said container being substantially impervious to said material, said container being hermetically sealed to allow heating or cooling of material in said container to form a heat sink; and insulation material around said container to control the rate of heat transfer to and from said material.

* * * * *